(12) United States Patent
Debinski et al.

(10) Patent No.: US 6,884,581 B2
(45) Date of Patent: Apr. 26, 2005

(54) METHOD FOR IDENTIFYING A TEST COMPOUND THAT MODULATES EXPRESSION OF A FRA-1 GENE IN A BRAIN CANCER CELL

(75) Inventors: Waldemar Debinski, Hershey, PA (US); Denise M. Gibo, Hershey, PA (US)

(73) Assignee: The Penn State Research Foundation, University Park, PA (US)

( * ) Notice: Subject to any disclaimer, the term of this patent is extended or adjusted under 35 U.S.C. 154(b) by 515 days.

(21) Appl. No.: 10/075,499

(22) Filed: Feb. 12, 2002

(65) Prior Publication Data

US 2002/0151457 A1 Oct. 17, 2002

Related U.S. Application Data

(60) Provisional application No. 60/268,089, filed on Feb. 12, 2001.

(51) Int. Cl.[7] ............................ C12Q 1/68; C12Q 1/02; G01N 33/53
(52) U.S. Cl. ............................ 435/6; 435/7.1; 435/29
(58) Field of Search ............................ 435/6, 7.1, 29

(56) References Cited

U.S. PATENT DOCUMENTS 6,124,133 A * 9/2000 Taylor et al. ............... 435/375

OTHER PUBLICATIONS

Bhattacharya et al., "Regualtion of the Urokinase–type Plasminogen Activator Receptor Gene in Different Grades of Human Glioma Cell Lines," Clinical Cancer Research, 7:267–276, 2001.
Won et al., "Stimulation of astrocyte–enriched culture with arachidonic acid increases proenkephalin mRNA: involvement of proto–oncoprotein and mitogen activated protein kinases," Molecular Brain Research, 76: 396–406, 2000.
Kustikova et al., "Fra–1 Induces Morphological Transformation and Increases In Vitro Invasiveness and Motility of Epitheliod Adenocarcinoma Cells," Molecular and Cellular Biology, 18: 7095–7105, 1998.
Chiappetta et al., "FRA–1 Expression in Hyperplastic and Neoplastic Thyroid Diseases[1]," Clinical Cancer Research, 6: 4300–4307, 2000.
Debinski et al., "VEGF–D is an X–linked/AP–1 Regulated Putative Onco–angiogen in Human Glioblastoma Multiforme," Molecular Medicine 7: 598–608, 2001.

* cited by examiner

Primary Examiner—Terry McKelvey
(74) Attorney, Agent, or Firm—Akerman Senterfitt

(57) ABSTRACT

Fra-1 serves as a target for diagnosing and treating glioblastoma multiforme and related brain cancers. Cancer in a brain tissue sample is detected by analyzing expression of Fra-1 in the sample. Brain cancer is treated by modulating Fra-1 gene expression in cells of the cancer, and by inhibiting angiogenesis associated with the cancer by interfering with Fra-1 binding to a VEGF-D promoter.

8 Claims, No Drawings

METHOD FOR IDENTIFYING A TEST COMPOUND THAT MODULATES EXPRESSION OF A FRA-1 GENE IN A BRAIN CANCER CELL

CROSS REFERENCE TO RELATED APPLICATION

The present application claims the priority of U.S. provisional patent application No. 60/268,089 filed Feb. 12, 2001.

FIELD OF THE INVENTION

The invention relates to the fields of medicine, angiogenesis and neuro-oncology. More particularly, the invention relates to compositions and methods for detecting and treating malignant tumors.

BACKGROUND OF THE INVENTION

Cancer is presently the second leading cause of death in developed nations. Wingo et al., J. Reg. Management, 25:43–51 (1998). Despite recent research that has revealed many of the molecular mechanisms of tumorigenesis, few new treatments have achieved widespread clinical success in treating solid tumors. Current treatments for most malignancies thus remain gross resection, chemotherapy, and radiotherapy. While increasingly successful, each of these treatments still causes numerous undesired side effects. The primary cause of these side effects is that none of these conventional methods specifically targets only diseased cells. For example, surgery results in pain, traumatic injury to healthy tissue, and scarring. Radiotherapy and chemotherapy cause nausea, immune suppression, gastric ulceration and secondary tumorigenesis.

In an effort to develop techniques to more specifically target diseased cells, progress in tumor immunology has led to the discovery of antigens that are preferentially or specifically expressed by cancer cells. The identification of tumor-specific cellular markers has proven extremely valuable for diagnosing and assessing the progression of certain types of tumors. Antibodies specific for tumor cell markers or ligands that bind specifically to a tumor cell receptor have been successfully used in diagnostics, including both the characterization of excised tissue samples and in vivo imaging. Tumor-specific antibodies and ligands have also been used in the targeted delivery of cytotoxic molecules to specific tumor cells. Some tumor cell antigens are known to function in the pathogenesis of a cancer. Modulating the function of these antigens could impair the progression of the disease.

SUMMARY

The invention relates to the discovery that glioblastoma multiforme (GBM) strongly expresses Fra-1, an AP-1 transcription factor. The gene for VEGF-D, a vascular endothelial growth factor that plays a role in angiogenesis, harbors an optimal AP-1 binding site within its promoter region. When heterodimerized with c-Jun, Fra-1 binds to the AP-1 site within the VEGF-D gene promoter and activates expression of VEGF-D. Based on this discovery, central nervous system (CNS) cancers such as GBM can be diagnosed and treated using Fra-1 as a target tumor antigen. In addition, by disrupting the interaction between Fra-1 and the VEGF-D gene promoter, tumor angiogenesis can be inhibited.

In addition to playing a role in angiogenesis, Fra-1 and other AP-1 regulated factors have been associated with tumor invasiveness. AP-1 induced constitutive gene expression that occurs in a transcription factor-specific manner in GBM contributes to the high neo-vascularization and invasiveness of this fatal brain tumor. Changes in a cell's phenotype due to expression of Fra-1, including anchorage-independent growth and invasiveness, can be evaluated in vitro. The motility of Fra-1 transfected cells may also be analyzed in vitro. Furthermore, AP-1 activity in Fra-1 transfected cells can be measured using an artificial AP-1 dependent promoter. Thus, Fra-1 can also serve as a target for inhibiting tumor invasiveness.

Accordingly, the invention features a method for detecting a cancer in a brain tissue sample (e.g., one isolated from a human subject). This method includes the steps of providing the brain tissue sample; and analyzing the brain tissue sample for a Fra-1 marker such as a Fra-1 nucleic acid or Fra-1 protein. In this method, the step of analyzing the brain tissue sample can include comparing the quantity of expression of the Fra-1 marker to a first sample known to express detectable levels of the Fra-1 marker (a positive control) and a second sample known to not express detectable levels of the Fra-1 marker (a negative control).

Fra-1 nucleic acid expression can be analyzed by isolating RNA from the tissue sample, generating cDNAs from the isolated RNA, amplifying the cDNAs by PCR to generate a PCR product. Alternatively, Fra-1 nucleic acid expression can be analyzed by isolating nucleic acid from the tissue sample, and contacting the isolated nucleic acid with an oligonucleotide probe (e.g., a labeled oligonucleotide probe) that hybridizes under stringent hybridization conditions to the Fra-1 nucleic acid.

Fra-1 protein expression can be analyzed by contacting at least a portion of the brain tissue sample with a probe that specifically binds to the Fra-1 protein. The probe can be an antibody (e.g., a polyclonal or monoclonal antibody), and can include a detectable label.

In another aspect, the invention features a method of modulating Fra-1 gene expression in a brain cancer cell. This method includes the steps of: providing a brain cancer cell that expresses a Fra-1 gene; and introducing into the cell an agent that modulates the expression of the Fra-1 gene in the cell. The agent can be an oligonucleotide such as an antisense oligonucleotide that hybridizes under stringent hybridization conditions to a polynucleotide that encodes a Fra-1 protein.

The invention also features a method of identifying a test compound that modulates expression of a Fra-1 gene in a brain cancer cell (e.g., one derived from a human brain). This method includes the steps of: providing a brain cancer cell expressing a Fra-1 gene; contacting the cell with the test compound; and detecting a modulation in the expression of the Fra-1 gene. Detecting the modulation indicates that the test compound modulates expression of the Fra-1 gene. Modulation in the expression of the Fra-1 gene can be assessed by analyzing the cell for a change in the amount of a Fra-1 marker in the cell.

Also within the invention is a method for inhibiting angiogenesis associated with a brain cancer in a subject. This method includes the steps of: providing an agent that interferes with Fra-1 binding to a VEGF-D gene promoter; and administering the agent to the central nervous system of the subject in an amount effective to inhibit blood vessel development associated with the brain cancer. The agent that interferes with Fra-1 binding to a VEGF-D gene promoter can be one that specifically binds a c-Jun protein, a Fra-1 protein, or a Fra-1 gene promoter. The agent can also be a variant of a native c-Jun protein that binds the Fra-1 protein but lacks the ability to bind a VEGF-D promoter; or a variant of a native Fra-1 protein that binds a c-Jun protein but lacks the ability to bind a VEGF-D promoter Unless otherwise defined, all technical terms used herein have the same meaning as commonly understood by one of ordinary skill in the art to which this invention belongs. Commonly understood definitions of molecular biology terms can be found in Rieger et al., Glossary of Genetics: Classical and Molecular, 5th edition, Springer-Verlag: New York, 1991; and Lewin, Genes V, Oxford University Press: New York, 1994.

By the term "cancer" is meant any disorder of cell growth that results in invasion and destruction of surrounding healthy tissue by abnormal cells.

As used herein, the term "promoter" refers to the general region of a DNA molecule that signals the start of transcription. It is this region to which an RNA polymerase binds and initiates transcription. Fra-1 protein, in concert with c-Jun protein, binds the VEGF-D gene promoter. The VEGF-D gene promoter is described in detail in Rocchigiani et al. Genomics 47:207–216 (1998). The VEGF-D gene promoter of the sequence deposited with GenBank as Accession No. Y12864 is denoted as nucleotides 1–465 (the exon 1 promoter).

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors."

A first nucleic acid sequence is "operably" linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein coding regions, in reading frame.

As used herein, the term "gene" means a nucleic acid molecule that codes for a particular protein, or in certain cases, a functional or structural RNA molecule. For example, a Fra-1 gene encodes a Fra-1 protein. The phrase "nucleic acid" or a "nucleic acid molecule" means a chain of two or more nucleotides such as RNA (ribonucleic acid) and DNA (deoxyribonucleic acid). A "purified" nucleic acid molecule is one that is substantially separated from other nucleic acid sequences in a cell or organism in which the nucleic acid naturally occurs (e.g., 30, 40, 50, 60, 70, 80, 90, 95, 96, 97, 98, 99, 100% free of contaminants). The term includes, e.g., a recombinant nucleic acid molecule incorporated into a vector, a plasmid, a virus, or a genome of a prokaryote or eukaryote. Examples of purified nucleic acids include cDNAs, fragments of genomic nucleic acids, nucleic acids produced polymerase chain reaction (PCR), nucleic acids formed by restriction enzyme treatment of genomic nucleic acids, recombinant nucleic acids, and chemically synthesized nucleic acid molecules. A "recombinant" nucleic acid molecule is one made by an artificial combination of two otherwise separated segments of sequence, e.g., by chemical synthesis or by the manipulation of isolated segments of nucleic acids by genetic engineering techniques.

The phrases "Fra-1 gene," "Fra-1 polynucleotide," or "Fra-1 nucleic acid" as used herein mean a native Fra-1-encoding nucleic acid sequence, e.g., the native human (Genbank Accession Nos. X16707 and D14493), rat (Accession Nos. V24154 and M19651), and mouse (Accession Nos. U34245 and AF017128) Fra-1 genes; a native form Fra-1 cDNA; a nucleic acid having sequences from which a Fra-1 cDNA can be transcribed; and/or allelic variants and homologs of the foregoing. The terms encompass double-stranded DNA, single-stranded DNA, and RNA.

As used herein, "protein" or "polypeptide" mean any peptide-linked chain of amino acids, regardless of length or post-translational modification, e.g., glycosylation or phosphorylation. A "purified" polypeptide is one that is substantially separated from other polypeptides in a cell or organism in which the polypeptide naturally occurs (e.g., 30, 40, 50, 60, 70, 80, 90, 95, 96, 97, 98, 99, 100% free of contaminants).

By the phrase "Fra-1 protein" or "Fra-1 polypeptide" is meant an expression product of a Fra-1 gene such as a native Fra-1 protein, or a protein that shares at least 65% (but preferably 75, 80, 85, 90, 95, 96, 97, 98, or 99%) amino acid sequence identity with one of the foregoing and displays a functional activity of a human native Fra-1 protein. A "functional activity" of a protein is any activity associated with the physiological function of the protein. For example, functional activities of a native Fra-1 protein may include binding c-Jun, binding a VEGF-D gene promoter, activating the VEGF-D gene, increased expression in certain neoplastic tissues, and the ability to stimulate angiogenesis.

When referring to a nucleic acid molecule or polypeptide, the term "native" refers to a naturally-occurring (e.g., a "wild-type") nucleic acid or polypeptide. A "homolog" of a Fra-1 gene from one species of organism is a gene sequence encoding a Fra-1 polypeptide isolated from an organism of a different species. Similarly, a "homolog" of a native Fra-1 polypeptide is an expression product of a Fra-1 gene homolog.

As used herein, a "Fra-1 marker" is any molecule whose presence in a sample (e.g., a cell) indicates that a Fra-1 gene is expressed in the sample. Fra-1 markers include Fra-1 nucleic acids and Fra-1 proteins. "Expressing a Fra-1 gene" or like phrases mean that a sample contains a transcription product (e.g., messenger RNA, i.e., "mRNA") of a Fra-1 gene or a translation product of a Fra-1 protein-encoding nucleic acid (e.g., a Fra-1 protein). A cell expresses a Fra-1 gene when it contains a detectable level of a Fra-1 nucleic acid or a Fra-1 protein.

A "fragment" of a Fra-1 nucleic acid is a portion of a Fra-1 nucleic acid that is less than full-length and comprises at least a minimum length capable of hybridizing specifically with a native Fra-1 nucleic acid under stringent hybridization conditions. The length of such a fragment is preferably at least 15 nucleotides, more preferably at least 20 nucleotides, and most preferably at least 30 nucleotides of a native Fra-1 nucleic acid sequence. A "fragment" of a Fra-1 polypeptide is a portion of a Fra-1 polypeptide that is less than full-length (e.g., a polypeptide consisting of 5, 10, 15, 20, 30, 40, 50, 75, 100 or more amino acids of a native Fra-1 protein), and preferably retains at least one functional activity of a native Fra-1 protein.

When referring to hybridization of one nucleic acid to another, "low stringency conditions" means in 10% formamide, 5× Denhart's solution, 6×SSPE, 0.2% SDS at 42° C., followed by washing in 1×SSPE, 0.2% SDS, at 50°

C.; "moderate stringency conditions" means in 50% formamide, 5× Denhart's solution, 5×SSPE, 0.2% SDS at 42° C., followed by washing in 0.2×SSPE, 0.2% SDS, at 65° C.; and "high stringency conditions" means in 50% formamide, 5× Denhart's solution, 5×SSPE, 0.2% SDS at 42° C., followed by washing in 0.1×SSPE, and 0.1% SDS at 65° C. The phrase "stringent hybridization conditions" means low, moderate, or high stringency conditions.

By the term "Fra-1-specific antibody" is meant an antibody that binds a Fra-1 protein and displays no substantial binding to other naturally occurring proteins other than those sharing the same antigenic determinants as the Fra-1 protein. The term includes polyclonal and monoclonal antibodies as well as antibody fragments. As used herein, "bind," "binds," or "interacts with" means that one molecule recognizes and adheres to a particular second molecule in a sample, but does not substantially recognize or adhere to other structurally unrelated molecules in the sample. Generally, a first molecule that "specifically binds" a second molecule has a binding affinity greater than about $10^5$ to $10^6$ moles/liter for that second molecule.

The term "labeled," with regard to a probe or antibody, is intended to encompass direct labeling of the probe or antibody by coupling (i.e., physically linking) a detectable substance to the probe or antibody.

Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. The particular embodiments discussed below are illustrative only and not intended to be limiting.

DETAILED DESCRIPTION

The invention provides methods and compositions for diagnosing and treating malignant tumors including, in particular, brain cancers such as GBM. For example, according to the invention, brain cancer is diagnosed by analyzing a brain tissue sample for expression of a Fra-1 marker, such as a Fra-1 nucleic acid or a Fra-1 protein. Brain cancer is treated by introducing into the cancer cells an agent that modulates Fra-1 gene expression in the cells. A brain cancer can also be treated by inhibiting the angiogenesis associated with the cancer by interfering with Fra-1 activation of a VEGF-D gene, e.g., by administering a molecule that interferes with the Fra-1/VEGF-D promoter or the Fra-1/c-Jun interaction to a subject suffering from a brain cancer. The invention also provides a method for identifying a test compound that modulates expression of a Fra-1 gene in a brain cancer cell. To identify such a compound, a brain cancer cell expressing a Fra-1 gene is contacted with a test compound and analyzed for modulations in Fra-1 expression.

The below described preferred embodiments illustrate adaptations of these compositions and methods. Nonetheless, from the description of these embodiments, other aspects of the invention can be made and/or practiced based on the description provided below.

Biological Methods

Methods involving conventional molecular biology techniques are described herein. Such techniques are generally known in the art and are described in detail in methodology treatises such as Molecular Cloning: A Laboratory Manual, 2nd ed., vol. 1–3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Various techniques using polymerase chain reaction (PCR) are described, e.g., in Innis et al., PCR Protocols: A Guide to Methods and Applications, Academic Press: San Diego, 1990. PCR-primer pairs can be derived from known sequences by known techniques such as using computer programs intended for that purpose (e.g., Primer, Version 0.5, © 1991, Whitehead Institute for Biomedical Research, Cambridge, Mass.). Methods for chemical synthesis of nucleic acids are discussed, for example, in Beaucage and Carruthers, Tetra. Letts. 22:1859–1862, 1981, and Matteucci et al., J. Am. Chem. Soc. 103:3185, 1981. Chemical synthesis of nucleic acids can be performed, for example, on commercial automated oligonucleotide synthesizers. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992. Conventional methods of gene transfer and gene therapy can also be adapted for use in the present invention. See, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; and Retro-vectors for Human Gene Therapy, ed. C. P. Hodgson, Springer Verlag, 1996.

Method of Detecting a Cancer

The invention provides a method for detecting a cancer in a brain tissue sample by analyzing the brain tissue sample for a Fra-1 marker such as a Fra-1 nucleic acid or Fra-1 protein. A preferred version of this method includes comparing the quantity of Fra-1 marker expression in the brain tissue sample to one or more control samples. The control samples can be a positive control sample, i.e., a sample known to express detectable levels of the Fra-1 marker using the same method of analysis as used for the brain tissue sample; and a negative control sample, i.e., a sample known not to express detectable levels of the Fra-1 marker using the same method of analysis as used for the brain tissue sample. Use of positive and negative controls ensures accuracy of test results.

Cancerous Tumors

The invention is based on the discovery that brain cancer cells express higher levels of Fra-1 than do normal brain cells and that Fra-1 activates VEGF-D gene expression. Accordingly, preferred methods of the invention involve analyzing the brain cancer cells, particularly glioma and GBM cells, for Fra-1 expression. Various forms of glioma/GBM are described in more detail in Dai and Holland, Biochim. Biophys. Acta, 1551 :M19–27, 2001 and Holland, Nat. Rev. Genetics, 2:120–129, 2001. In addition to brain cancers, the methods and compositions described herein might be used with other types of cancers that express high levels of Fra-1 and VEGF-D.

Brain Tissue Samples

The invention provides methods for analyzing a brain tissue sample and administering a composition to a brain cancer in a mammal. Surgical techniques for obtaining brain tissue samples as well as administering various compositions to the brain are well known in the art. For example, such methods are described in standard neuro-surgery texts such as Atlas of Neurosurgery: Basic Approaches to Cranial and Vascular Procedures, by F. Meyer, Churchill Livingstone, 1999; Stereotactic and Image Directed Surgery of Brain Tumors, 1st ed., by David G. T. Thomas, WB Saunders Co., 1993; and Cranial Microsurgery: Approaches and Techniques, by L. N. Sekhar and E. De Oliveira, 1st ed., Thieme Medical Publishing, 1999. Methods for obtaining and analyzing brain tissue are also described in Belay et al., Arch. Neurol. 58: 1673–1678 (2001); and Seijo et al., J. Clin. Microbiol. 38: 3892–3895 (2000).

Detection of Fra-1 Polynucleotides and Proteins

The invention encompasses methods for detecting the presence of a Fra-1 marker such as a Fra-1 protein or a Fra-1 nucleic acid in a biological sample as well as methods for measuring the level of a Fra-1 marker in a biological sample. Such methods are useful for diagnosing cancer associated with Fra-1 expression, e.g., brain cancer.

An exemplary method for detecting the presence or absence of a Fra-1 protein or nucleic acid in a biological sample involves obtaining a biological sample from a subject (e.g., a human patient), contacting the biological sample with a compound or an agent capable of detecting a Fra-1 protein or a nucleic acid encoding a Fra-1 protein (e.g., antibody, mRNA or genomic DNA), and analyzing binding of the compound or agent to the sample after washing. Those samples having specifically bound compound or agent express a Fra-1 protein or a nucleic acid encoding a Fra-1 protein.

A preferred agent for detecting a nucleic acid encoding a Fra-1 protein is a labeled nucleic acid probe capable of hybridizing to the nucleic acid encoding the Fra-1 protein. The nucleic acid probe can be, for example, all or a portion of a Fra-1 gene itself or all or a portion of a complement of a Fra-1 gene. Similarly, the probe can also be all or a portion of a Fra-1 gene variant, or all or a portion of a complement of a Fra-1 gene variant. For instance, oligonucleotides at least 15, 30, 50, 100, 250, or 500 nucleotides in length that specifically hybridize under stringent conditions to a native Fra-1 nucleic acid or a complement of a native Fra-1 nucleic acid can be used as probes within the invention. A preferred agent for detecting a Fra-1 protein is an antibody capable of binding to a Fra-1 protein, preferably an antibody with a detectable label. Such antibodies can be polyclonal, or more preferably, monoclonal. An intact antibody, or a fragment thereof (e.g., Fab or F(ab')$_2$) can be used.

Methods of the invention can be used to detect an mRNA encoding a Fra-1 protein, a genomic DNA encoding a Fra-1 protein, or a Fra-1 protein in a biological sample in vitro as well as in vivo. The quantity of expression of Fra-1 marker from a brain tissue sample may be compared with appropriate controls such as a first sample known to express detectable levels of the Fra-1 marker (i.e., a positive control) and a second sample known to not express detectable levels of the Fra-1 marker (i.e., a negative control). For example, in vitro techniques for detection of mRNAs encoding a Fra-1 protein include PCR amplification methods, Northern hybridizations, and in situ hybridizations. In vitro techniques for detection of a Fra-1 protein include enzyme linked immunosorbent assays (ELISAs), Western blots, immuno-precipitations and immunofluorescence. In vitro techniques for detection of genomic DNA encoding Fra-1 include Southern hybridizations. Furthermore, in vivo techniques for detection of a Fra-1 protein include introducing a labeled anti-Fra-1 antibody into a biological sample or test subject. For example, the antibody can be labeled with a radioactive marker whose presence and location in a biological sample or test subject can be detected by standard imaging techniques.

Myriad detectable labels that may be used in a diagnostic assay for Fra-1 expression are known in the art. Nucleic acid probes, for example, may be labeled with chemiluminescent or radioactive substance. The amount of labeled probe bound to a Fra-1 marker may then be assessed using photographic or X-ray film or other suitable methods for detecting luminescence or radioactivity. Antibodies used in methods for detecting Fra-1 protein may be conjugated to a detectable label, e.g., an enzyme such as horseradish peroxidase. Antibodies labeled with horseradish peroxidase can be detected by adding an appropriate substrate that produces a color change in the presence of horseradish peroxidase. Several other detectable labels that may be used are known. Common examples of these include alkaline phosphatase, horseradish peroxidase, fluorescent compounds, luminescent compounds, colloidal gold, magnetic particles, biotin, radioisotopes, and enzymes.

Nucleic Acids Encoding Fra-1 Proteins

Methods of the present invention relate to Fra-1 nucleic acids. Preferred nucleic acid molecules for use in the invention include native human (Genbank Accession Nos. X16707 and D14493), rat (U24154 and M19651), and mouse (U34245 and AF017128) Fra-1 polynucleotides. Nucleic acid molecules utilized in the present invention may be in the form of RNA or in the form of DNA (e.g., cDNA, genomic DNA, and synthetic DNA). The DNA may be double-stranded or single-stranded, and if single-stranded may be the coding (sense) strand or non-coding (anti-sense) strand. In addition to a coding sequence which encodes a native Fra-1 protein, other nucleic acid molecules that can be used in the invention include variants of a native Fra-1 gene such as those that encode fragments, analogs and derivatives of a native Fra-1 protein. Such variants may be, e.g., a naturally occurring allelic variant of a native Fra-1 gene or a homolog of a native Fra-1 gene.

Vectors encoding a native or variant Fra-1, Fra-1 binding species, c-Jun binding species, or antisense construct can be generated by recombinant DNA technology methods that are known in the art. Suitable vectors include plasmid vectors, viral vectors, or other types of vectors known or newly discovered in the art. The criterion for use is only that the vector be capable of replicating and expressing a native or variant Fra-1 protein, Fra-1 binding species, c-Jun binding species, or antisense construct sequence. Expression of the sequence encoding native a or variant Fra-1 protein, Fra-1 binding species, c-Jun binding species, or antisense construct can be directed by any promoter known in the art to act in mammalian, and preferably in human, cells. Such promoters can be inducible or constitutively active and include but are not limited to: the SV40 early promoter region (Bemoist et al., Nature 290:304, 1981); the promoter contained in the 3' long terminal repeat of Rous Sarcoma virus (Yamamoto et al., Cell 22:787–797, 1988); the herpes thymidine kinase promoter (Wagner et al., PNAS 78:1441, 1981); or the regulatory sequences of the metallothionein gene (Brinster et al., Nature 296:39, 1988).

Vectors utilized in methods of the invention to deliver a native or variant Fra-1 protein, Fra-1 binding species, c-Jun binding species, or antisense construct may also contain, if desired, regulatory elements such as a tissue-specific promoter or enhancer, a transcription initiation start site, a ribosomal binding site, an RNA processing signal, a transcription termination site, and/or a polyadenylation signal. Tissue-specific promoters and enhancers used in methods of the invention may include those that direct gene expression specifically in CNS tissue, and more preferably in cells of astrocyte lineage. An example of a neuron and astrocyte-specific promoter is the proximal region of the c-fos promoter. Onteniente et al., Brain Res. Mol. Brain Res. 21:225–234 (1994). Another example of a promoter that directs astrocyte-specific gene expression is the human glial fibrillary acidic protein (hGFAP) promoter. Ding et al., Cancer Res. 61: 3826–3836 (2001); and Vandier et al., Cancer Gene Therapy 7:1120–1126 (2000). Examples of enhancers that direct high-level and specific gene expression in astrocytes are two apoE gene enhancers that are located downstream of the apoE gene. Greham et al., J. Neurosci. 21: 812–822 (2001).

Probes and Primers

Nucleic acids that hybridize under stringent conditions to Fra-1 nucleic acid or the complement of Fra-1 nucleic acid can be used in the invention. For example, such nucleic acids can be those that hybridize to Fra-1 nucleic acid or the complement of a Fra-1 nucleic acid under low stringency conditions, moderate stringency conditions, or high stringency conditions. Preferred such nucleic acids are those having a nucleotide sequence that is the complement of all or a portion of Fra-1 nucleic acid. Others that might be used include polynucleotides that share at least 65% (e.g., 65, 70, 75, 80, 85, 90, 91, 92, 93, 94, 95, 96, 97, 98, and 99%) sequence identity to a native Fra-1 nucleic acid or the complement of Fra-1 nucleic acid. Nucleic acids that hybridize under stringent conditions to or share at least 65% sequence identity with Fra-1 nucleic acid or the complement of Fra-1 nucleic acid can be obtained by techniques known in the art such as by making mutations in a native Fra-1 gene, or by isolation from an organism expressing such a nucleic acid (e.g., an allelic variant).

Methods of the invention utilize oligonucleotide probes (i.e., isolated nucleic acid molecules conjugated with a detectable label or reporter molecule, e.g., a radioactive isotope, ligand, chemiluminescent agent, or enzyme); and oligonucleotide primers (i.e., isolated nucleic acid molecules that can be annealed to a complementary target DNA strand by nucleic acid hybridization to form a hybrid between the primer and the target DNA strand, then extended along the target DNA strand by a polymerase, e.g., a DNA polymerase). Primer pairs can be used for amplification of a nucleic acid sequence, e.g., by the polymerase chain reaction (PCR) or other conventional nucleic-acid amplification methods.

PCR primers can be used to amplify Fra-1 nucleic acids using known PCR and RT-PCR protocols. Such primers can be designed according to known methods as PCR primer design is generally known in the art. See, e.g., methodology treatises such as Basic Methods in Molecular Biology, 2nd ed., ed. Davis et al., Appleton & Lange, Norwalk, Conn., 1994; and Molecular Cloning: A Laboratory Manual, 2nd ed., vol.1–3, ed. Sambrook et al., Cold Spring Harbor Laboratory Press, Cold Spring Harbor, N.Y., 1989. PCR primer pairs previously used to amplify a Fra-1 nucleic acid sequence are described in Hu et al., Clin. Cancer Res. 7:2213–2221 (2001); and Chiappetta et al., Clin. Cancer Res. 6:4300–4306 (2000).

Probes and primers utilized in methods of the invention are generally 15 nucleotides or more in length, preferably 20 nucleotides or more, more preferably 25 nucleotides, and most preferably 30 nucleotides or more. Preferred probes and primers are those that hybridize to a native Fra-1 gene (or cDNA or mRNA) sequence under high stringency conditions, and those that hybridize to Fra-1 gene homologs under at least moderately stringent conditions. Preferably, probes and primers according to the present invention have complete sequence identity with a native Fra-1 nucleic acid sequence. However, probes differing from this sequence that retain the ability to hybridize to a native Fra-1 gene sequence under stringent conditions may be designed by conventional methods and used in the invention. Primers and probes based on the Fra-1 gene sequences disclosed herein can be used to confirm (and, if necessary, to correct) the disclosed Fra-1 gene sequences by conventional methods, e.g., by re-cloning and sequencing a native Fra-1 gene or cDNA.

Fra-1 Proteins

The invention also provides methods involving Fra-1 proteins. Fra-1, also known as fos-related antigen-1, is found to be expressed at higher levels in GBM cells, such as G48a, when compared with normal human tissue. The Fra-1 protein is approximately 42 kDa and is localized to the nucleus, which would be expected for a transcription factor.

Methods of the present invention may utilize a purified Fra-1 protein encoded by a nucleic acid of the invention. A preferred form of Fra-1 is a purified native human Fra-1 protein that has the amino acid sequence deposited with NCBI as accession No. NP005429. Other forms of Fra-1 include those of mouse (SwissProt accession No. P48755) and rat (SwissProt accession No. P10158).

Variants of native Fra-1 proteins such as fragments, analogs and derivatives of native Fra-1 proteins may also be used in methods of the invention. Such variants include, e.g., a polypeptide encoded by a naturally occurring allelic variant of a native Fra-1 gene, a polypeptide encoded by an alternative splice form of a native Fra-1 gene, a polypeptide encoded by a homolog of a native Fra-1 gene, and a polypeptide encoded by a non-naturally occurring variant of a native Fra-1 gene.

Fra-1 protein variants have a peptide sequence that differs from a native Fra-1 protein in one or more amino acids. The peptide sequence of such variants can feature a deletion, addition, or substitution of one or more amino acids of a native Fra-1 polypeptide. Amino acid insertions are preferably of about 1 to 4 contiguous amino acids, and deletions are preferably of about 1 to 10 contiguous amino acids. In some applications, variant Fra-1 proteins substantially maintain a native Fra-1 protein functional activity (e.g., association with cancer or ability to modulate angiogenesis). For other applications, variant Fra-1 proteins lack or feature a significant reduction in a Fra-1 protein functional activity. Where it is desired to retain a functional activity of native Fra-1 protein, preferred Fra-1 protein variants can be made by expressing nucleic acid molecules within the invention that feature silent or conservative changes. Variant Fra-1 proteins with substantial changes in functional activity can be made by expressing nucleic acid molecules within the invention that feature less than conservative changes.

Fra-1 protein fragments corresponding to one or more particular motifs and/or domains or to arbitrary sizes, for example, at least 5, 10, 25, 50, 75, 100, 125, 150, 175, 200, and 250 amino acids in length may be utilized in methods of the present invention. Isolated peptidyl portions of Fra-1 proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a Fra-1 protein used in methods of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a native Fra-1 protein.

Methods of the invention may also involve recombinant forms of the Fra-1 proteins. Recombinant polypeptides preferred by the present invention, in addition to native Fra-1 protein, are encoded by a nucleic acid that has at least 85% sequence identity (e.g., 85, 86, 87, 88, 89, 90, 91, 92, 93, 94, 95, 96, 97, 98, 99, 100%) with a native Fra-1 nucleic acid sequence. In a preferred embodiment, variant Fra-1 proteins lack one or more functional activities of native Fra-1 protein (e.g., binding c-Jun and activating VEGF-D gene expression).

Fra-1 protein variants can be generated through various techniques known in the art. For example, Fra-1 protein variants can be made by mutagenesis, such as by introducing discrete point mutation(s), or by truncation. Mutation can give rise to a Fra-1 protein variant having substantially the same, or merely a subset of the functional activity of a native Fra-1 protein. Alternatively, antagonistic forms of the protein can be generated which are able to inhibit the function of the naturally occurring form of the protein, such as by competitively binding to another molecule that interacts with Fra-1 protein. In addition, agonistic forms of the protein may be generated that constitutively express one or more Fra-1 functional activities. Other variants of Fra-1 proteins that can be generated include those that are resistant to proteolytic cleavage, as for example, due to mutations that alter protease target sequences. Whether a change in the amino acid sequence of a peptide results in a Fra-1 protein variant having one or more functional activities of a native Fra-1 protein can be readily determined by testing the variant for a native Fra-1 protein functional activity.

Nucleic acid molecules encoding Fra-1 fusion proteins may be used in methods of the invention. Such nucleic acids can be made by preparing a construct (e.g., an expression vector) that expresses a Fra-1 fusion protein when introduced into a suitable host. For example, such a construct can be made by ligating a first polynucleotide encoding a Fra-1 protein fused in frame with a second polynucleotide encoding another protein such that expression of the construct in a suitable expression system yields a fusion protein.

As another example, Fra-1 protein variants can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential Fra-1 protein sequences. The synthesis of degenerate oligonucleotides is well known in the art (see for example, Narang, S A (1983) Tetrahedron 39:3; Itakura et al. (1981) Recombinant DNA, Proc 3rd Cleveland Sympos. Macromolecules, ed. A G Walton, Amsterdam: Elsevier pp 273–289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386–390; Roberts et al. (1992) Proc. Natl. Acad. Sci. USA 89:2429–2433; Devlin et al. (1990) Science 249: 404–406; Cwirla et al. (1990) Proc. Natl. Acad. Sci. USA 87: 6378–6382; as well as U.S. Pat. Nos. 5,223,409; 5,198,346; and 5,096,815).

Similarly, a library of coding sequence fragments can be provided for a Fra-1 gene clone in order to generate a variegated population of Fra-1 protein fragments for screening and subsequent selection of fragments having one or more native Fra-1 protein functional activities. A variety of techniques are known in the art for generating such libraries, including chemical synthesis. In one embodiment, a library of coding sequence fragments can be generated by (i) treating a double-stranded PCR fragment of a Fra-1 gene coding sequence with a nuclease under conditions wherein nicking occurs only about once per molecule; (ii) denaturing the double-stranded DNA; (iii) renaturing the DNA to form double-stranded DNA which can include sense/antisense pairs from different nicked products; (iv) removing single-stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of Fra-1 gene variants. The most widely used techniques for screening large gene libraries typically involve cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

Combinatorial mutagenesis has a potential to generate very large libraries of mutant proteins, e.g., in the order of $10^{26}$ molecules. To screen a large number of protein mutants, techniques that allow one to avoid the very high proportion of non-functional proteins in a random library and simply enhance the frequency of functional proteins (thus decreasing the complexity required to achieve a useful sampling of sequence space) can be used. For example, recursive ensemble mutagenesis (REM), an algorithm that enhances the frequency of functional mutants in a library when an appropriate selection or screening method is employed, might be used. Arkin and Yourvan (1992) Proc. Natl. Acad. Sci. USA 89:7811–7815; Yourvan et al. (1992) Parallel Problem Solving from Nature, 2., In Maenner and Manderick, eds., Elsevier Publishing Co., Amsterdam, pp. 401–410; Delgrave et al. (1993) Protein Engineering 6(3):327–331.

Methods of the invention may utilize mimetics, e.g. peptide or non-peptide agents, that are able to disrupt binding of a Fra-1 protein to other proteins or molecules with which a native Fra-1 protein interacts. Thus, the mutagenic techniques described herein can also be used to map which determinants of Fra-1 protein participate in the intermolecular interactions involved in, for example, binding of a Fra-1 protein to other proteins which may function upstream (e.g., activators or repressors of Fra-1 functional activity) of the Fra-1 protein or to proteins or nucleic acids which may function downstream of the Fra-1 protein (e.g. VEGF-D promoter), and whether such molecules are positively or negatively regulated by the Fra-1 protein. To illustrate, the critical residues of a Fra-1 protein which are involved in molecular recognition of, for example, the Fra-1 protein or other components upstream or downstream of the Fra-1 protein can be determined and used to generate Fra-1 protein-derived peptidomimetics which competitively inhibit binding of the Fra-1 protein to that moiety. By employing scanning mutagenesis to map the amino acid residues of a Fra-1 protein that are involved in binding other proteins (e.g., c-Jun), peptidomimetic compounds can be generated which mimic those residues of a native Fra-1 protein. Such mimetics may then be used to interfere with the normal function of a Fra-1 protein. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopepitides (Ewenson et al. (1986) J. Med. Chem. 29:295; and Ewenson et al. in Peptides: Structure and Function (Proceedings of the 9th American Peptide Symposium) Pierce Chemical Co. Rockland, Ill., 1985), eta-turn dipeptide cores (Nagai et al. (1985) Tetrahedron Lett 26:647; and Sato et al. (1986) J. Chem. Soc. Perkin. Trans. 1:1231), and beta-aminoalcohols (Gordon et al. (1985) Biochem. Biophys. Res. Commun. 126:419; and Dann et al. (1986) Biochem. Biophys. Res. Commun. 134:71). Fra-1 proteins may also be chemically modified to create Fra-1 protein derivatives by forming covalent or aggregate conjugates with other chemical moieties, such as glycosyl groups, lipids, phosphate, acetyl groups and the like. Covalent derivatives of Fra-1 protein can be prepared by linking the chemical moieties to functional groups on amino acid side chains of the protein or at the N-terminus or at the C-terminus of the polypeptide.

Antibodies

Antibodies that specifically bind Fra-1 proteins can be used in methods of the invention, for example, in the detection of Fra-1 protein markers. Polyclonal antibodies are heterogeneous populations of antibody molecules that are contained in the sera of immunized animals. Antibodies used in methods of the invention include polyclonal antibodies and, in addition, monoclonal antibodies, single chain antibodies, Fab fragments, F(ab')$_2$ fragments, and molecules produced using a Fab expression library. Monoclonal antibodies, which are homogeneous populations of antibodies to a particular antigen, can be prepared using the Fra-1 proteins described above and standard hybridoma technology (see, for example, Kohler et al., Nature 256:495, 1975; Kohler et al., Eur. J. Immunol. 6:511, 1976; Kohler et al., Eur. J. Immunol. 6:292, 1976; Hammerling et al., "Monoclonal Antibodies and T Cell Hybridomas," Elsevier, N.Y., 1981; Ausubel et al., supra). In particular, monoclonal antibodies can be obtained by any technique that provides for the production of antibody molecules by continuous cell lines in culture such as described in Kohler et al., Nature 256:495, 1975, and U.S. Pat. No. 4,376,110; the human B-cell hybridoma technique (Kosbor et al., Immunology Today 4:72, 1983; Cole et al., Proc. Natl. Acad. Sci. USA 80:2026, 1983), and the EBV-hybridoma technique (Cole et al., "Monoclonal Antibodies and Cancer Therapy," Alan R. Liss, Inc., pp. 77–96, 1983). Such antibodies can be of any immunoglobulin class including IgG, IgM, IgE, IgA, IgD and any subclass thereof.

Antibodies that specifically recognize and bind to Fra-1 are useful in methods of the present invention. For example, such antibodies can be used in an immunoassay to monitor the level of a Fra-1 protein produced by a mammal (e.g., to determine the amount or subcellular location of a Fra-1 protein). Methods of the invention may also utilize antibodies, for example, in the detection of a Fra-1 protein in a biological sample. Antibodies also can be used in a screening assay to measure the effect of a candidate compound on expression or localization of a Fra-1 protein.

Modulating Fra-1 Expression Antisense, Ribozyme, Triplex Techniques

Another aspect of the invention relates to the use of purified antisense nucleic acids to inhibit expression of Fra-1. Antisense nucleic acid molecules within the invention are those that specifically hybridize (e.g. bind) under cellular conditions to cellular mRNA and/or genomic DNA encoding a Fra-1 protein in a manner that inhibits expression of the Fra-1 protein, e.g., by inhibiting transcription and/or translation. The binding may be by conventional base pair complementarity, or, for example, in the case of binding to DNA duplexes, through specific interactions in the major groove of the double helix.

Antisense constructs can be delivered, for example, as an expression plasmid which, when transcribed in the cell, produces RNA which is complementary to at least a unique portion of the cellular mRNA which encodes a Fra-1 protein. Alternatively, the antisense construct can take the form of an oligonucleotide probe generated ex vivo which, when introduced into a Fra-1 protein expressing cell, causes inhibition of Fra-1 protein expression by hybridizing with an mRNA and/or genomic sequences coding for Fra-1 protein. Such oligonucleotide probes are preferably modified oligonucleotides that are resistant to endogenous nucleases, e.g. exo-nucleases and/or endonucleases, and are therefore stable in vivo. Exemplary nucleic acid molecules for use as antisense oligonucleotides are phosphoramidate, phosphothioate and methylphosphonate analogs of DNA (see, e.g., U.S. Pat. Nos. 5,176,996; 5,264,564; and 5,256,775). Additionally, general approaches to constructing oligomers useful in antisense therapy have been reviewed, for example, by Van der Krol et al. (1988) Biotechniques 6:958–976; and Stein et al. (1988) Cancer Res 48:2659–2668. With respect to antisense DNA, oligodeoxyribonucleotides derived from the translation initiation site, e.g., between the −10 and +10 regions of a Fra-1 protein encoding nucleotide sequence, are preferred.

Antisense approaches involve the design of oligonucleotides (either DNA or RNA) that are complementary to Fra-1 mRNA. The antisense oligonucleotides will bind to Fra-1 mRNA transcripts and prevent translation. Absolute complementarity, although preferred, is not required. The ability to hybridize will depend on both the degree of complementarity and the length of the antisense nucleic acid. Generally, the longer the hybridizing nucleic acid, the more base mismatches with an RNA it may contain and still form a stable duplex or triplex. One skilled in the art can ascertain a tolerable degree of mismatch by use of standard procedures to determine the melting point of the hybridized complex. Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. (Wagner, R. (1994) Nature 372:333). Therefore, oligonucleotides complementary to either the 5' or 3' untranslated, non-coding regions of a Fra-1 gene could be used in an antisense approach to inhibit translation of endogenous Fra-1 mRNA. Oligonucleotides complementary to the 5' untranslated region of the mRNA should preferably include the complement of the AUG start codon. Although antisense oligonucleotides complementary to mRNA coding regions are generally less efficient inhibitors of translation, these could still be used in the invention. Whether designed to hybridize to the 5', 3' or coding region of a Fra-1 mRNA, preferred antisense nucleic acids are less that about 100 (e.g., less than about 30, 25, 20, or 18) nucleotides in length. Generally, in order to be effective, the antisense oligonucleotide should be 18 or more nucleotides in length.

Specific antisense oligonucleotides can be tested for effectiveness using in vitro studies to assess the ability of the antisense oligonucleotide to inhibit gene expression. Preferably such studies (1) utilize controls (e.g., a non-antisense oligonucleotide of the same size as the antisense oligonucleotide) to distinguish between antisense gene inhibition and nonspecific biological effects of oligonucleotides, and (2) compare levels of the target RNA or protein with that of an internal control RNA or protein.

Antisense oligonucleotides of the invention may include at least one modified base or sugar moiety. Exemplary modified bases include 5-fluorouracil, 5-bromouracil, 5-chlorouracil, 5-iodouracil, hypoxanthine, xanthine, 4-acetylcytosine, 5-(carboxyhydroxyethyl) uracil, 5-carboxymethylaminomethyl-2-thiouridine, 5-carboxymethylaminomethyluracil, dihydrouricil, beta-D-galactosylqueosine, inosine, N6-isopentenyladenine, 1-methylguanine, 1-methylinosine, 2,2-idimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Exemplary modified sugar moieties include arabinose, 2-fluoroarabinose, xylulose, and hexose. The antisense oligonucleotides of the invention may in some embodiments include at least one modified phosphate backbone such as a phosphorothioate, a phosphorodithioate, a phosphoramidothioate, a phosphoramidate, a phosphordiamidate, a methylphosphonate, an alkyl phosphotriester, or a formacetal or analog thereof.

Antisense oligonucleotides within the invention might also be an alpha-anomeric oligonucleotide. See, Gautier et al. (1987) Nucl. Acids Res. 15:6625–6641. For example, the antisense oligonucleotide can be a 2'-0-methylribonucleotide (Inoue et al. (1987) Nucl. Acids Res. 15:6131–6148), or a chimeric RNA-DNA analogue (Inoue et al. (1987) FEBS Lett. 215:327–330). Oligonucleotides of the invention may be synthesized by standard methods known in the art, e.g. by use of an automated DNA synthesizer. Phosphorothioate oligonucleotides may be synthesized by the method of Stein et al. (1988) Nucl. Acids Res. 16:3209). Methylphosphonate oligonucleotides can be prepared by use of controlled pore glass polymer supports (Sarin et al. (1988) Proc. Natl. Acad. Sci. U.S.A. 85:7448–7451).

Methods of the invention also utilize techniques for delivering one or more of the above-described nucleic acid molecules into cells that express Fra-1. A number of methods have been developed for delivering antisense DNA or RNA into cells. For instance, antisense molecules can be introduced directly into a cell by electroporation, liposome-mediated transfection, CaCl-mediated transfection, viral vector infection, or using a gene gun. Modified nucleic acid molecules designed to target the desired cells (e.g., antisense oligonucleotides linked to peptides or antibodies that specifically bind receptors or antigens expressed on the target cell surface) can be used. To achieve high intracellular concentrations of antisense oligonucleotides (as may be required to suppress translation on endogenous mRNAs), a preferred approach utilizes a recombinant DNA construct in which the antisense oligonucleotide is placed under the control of a strong promoter (e.g., the CMV promoter).

Ribozyme molecules designed to catalytically cleave Fra-1 mRNA transcripts can also be used to prevent translation of Fra-1 mRNAs and expression of Fra-1 proteins (See, e.g., Wright and Kearney, Cancer Invest. 19:495, 2001; Lewin and Hauswirth, Trends Mol. Med. 7:221, 2001; Sarver et al. (1990) Science 247:1222–1225 and U.S. Pat. No. 5,093,246). As one example, hammerhead ribozymes that cleave mRNAs at locations dictated by flanking regions that form complementary base pairs with the target mRNA might be used so long as the target mRNA has the following common sequence: 5'-UG-3'. See, e.g., Haseloff and Gerlach (1988) Nature 334:585–591. To increase efficiency and minimize the intracellular accumulation of non-functional mRNA transcripts, a ribozyme should be engineered so that the cleavage recognition site is located near the 5' end of the target Fra-1 mRNA. Ribozymes within the invention can be delivered to a cell using a vector as described below.

Other methods can also be used to reduce Fra-1 gene expression in a cell. For example, Fra-1 gene expression can be reduced by inactivating or "knocking out" the Fra-1 gene or its promoter using targeted homologous recombination. See, e.g., Kempin et al., Nature 389: 802 (1997); Smithies et al. (1985) Nature 317:230–234; Thomas and Capecchi (1987) Cell 51:503–512; and Thompson et al. (1989) Cell 5:313–321. For instance, a mutant, non-functional Fra-1 gene variant (or a completely unrelated DNA sequence) flanked by DNA homologous to the endogenous Fra-1 gene (either the coding regions or regulatory regions of the Fra-1 gene) can be used, with or without a selectable marker and/or a negative selectable marker, to transfect cells that express Fra-1 protein in vivo.

Fra-1 gene expression might also be reduced by targeting deoxyribonucleotide sequences complementary to the regulatory region of the Fra-1 gene (i.e., the Fra-1 promoter and/or enhancers) to form triple helical structures that prevent transcription of the Fra-1 gene in target cells. See generally, Helene, C. (1991) Anticancer Drug Des. 6(6):569–84; Helene, C., et al. (1992) Ann. N.Y. Acad. Sci. 660:27–36; and Maher, L. J. (1992) Bioassays 14(2):807–15. Nucleic acid molecules to be used in this technique are preferably single stranded and composed of deoxyribonucleotides. The base composition of these oligonucleotides should be selected to promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex. The potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

The antisense RNA and DNA, ribozyme, and triple helix molecules that can be used with methods of the invention may be prepared by any method known in the art for the synthesis of DNA and RNA molecules. These include techniques for chemically synthesizing oligodeoxyribonucleotides and oligoribonucleotides well known in the art such as for example solid phase phosphoramide chemical synthesis. RNA molecules may be generated by in vitro and in vivo transcription of DNA sequences encoding the antisense RNA molecule. Such DNA sequences may be incorporated into a wide variety of vectors which incorporate suitable RNA polymerase promoters. Alternatively, antisense cDNA constructs that synthesize antisense RNA constitutively or inducibly, depending on the promoter used, can be introduced stably into cell lines.

Inhibiting VEGF-D Expression

Methods that can be used to reduce VEGF-D expression include modulating the expression and activity of Fra-1. The gene for VEGF-D harbors an optimal AP-1 binding site in its promoter region and is activated by Fra-1, an AP-1 transcription factor. Accordingly, one may modulate VEGF-D expression by interfering with the binding of the Fra-1 protein to the VEGF-D promoter.

More particularly, methods of the invention may involve targeting the interaction of Fra-1 with its binding partners in an effort to block activation of the VEGF-D promoter by Fra-1. Fra-1 cannot activate gene expression itself, as it requires heterodimerization with Jun proteins to do so. c-Jun and JunB in particular are preferable partners for Fra-1 and, in the process of Fra-1 upregulation in response to Ras activation, c-Jun is primarily utilized as the binding partner with Fra-1. Therefore, nucleic acids which encode proteins that bind Fra-1 and preclude binding of Fra-1 to c-Jun may be used to block activation of the VEGF-D promoter by Fra-1. Methods of the invention may alternatively utilize mimetics, e.g. peptide or non-peptide agents, that are able to disrupt binding of a Fra-1 protein to other proteins or molecules (e.g., c-Jun) with which the native Fra-1 protein interacts. Alternatively, antagonistic forms of the Fra-1 protein can be generated which are able to inhibit the function of the naturally occurring form of the protein, such as by competitively binding to another molecule that interacts with Fra-1 protein. In particular, a variant form of Fra-1 that is able to heterodimerize with c-Jun yet is incapable of binding the VEGF-D promoter is suitable for use in a method to inhibit VEGF-D gene expression. Similarly, a variant form of c-Jun that is able to heterodimerize with Fra-1 yet is incapable of binding the VEGF-D promoter is suitable for use in a method to inhibit VEGF-D gene expression. Fra-1 and c-Jun protein variants can be generated through various techniques known in the art. For example, Fra-1 and c-Jun protein variants can be made by mutagenesis, such as by introducing an insertion, deletion or a discrete point mutation(s).

Gene Therapy

Methods of the present invention include the delivery of nucleic acids and proteins into a mammalian subject for inhibiting angiogenesis or otherwise treating a cancer. Gene therapy can be defined as the treatment of inherited or acquired diseases by the introduction and expression of genetic information in cells. Methods and compositions involving gene therapy vectors are described herein. Such techniques are generally known in the art and are described in methodology references such as Viral Vectors, eds. Yakov Gluzman and Stephen H. Hughes, Cold Spring Harbor Laboratory Press, Cold Spring Harbor, N.Y., 1988; Retroviruses, Cold Spring Harbor Laboratory Press, Plainview, N.Y., 2000; Gene Therapy Protocols (Methods in Molecular Medicine), ed. Jeffrey R. Morgan, Humana Press, Totawa, N.J., 2001; and Molecular Cloning: A Laboratory Manual, 2nd ed., vol. 1–3, ed. Sambrook et al., Cold Spring Harbor Laboratory Press, Cold Spring Harbor, N.Y., 1989.

Methods for inhibiting angiogenesis include anti-angiogenic agents that may be administered to a mammalian subject, including a human, by any suitable technique. Various techniques using viral vectors for the introduction of nucleic acids encoding a Fra-1 variant, Fra-1 binding species, c-Jun binding species, and antisense constructs into cells may be utilized in methods of the invention. Viruses are naturally evolved vehicles which efficiently deliver their genes into host cells and therefore are desirable vector systems for the delivery of therapeutic genes. Preferred viral vectors exhibit low toxicity to the host cell and produce therapeutic quantities of anti-angiogenic compounds in a tissue-specific manner. Viral vector methods and protocols are reviewed in Kay et al. Nature Medicine 7:33–40, 2001.

Methods for use of recombinant Adenoviruses as gene therapy vectors are discussed, for example, in W. C. Russell, Journal of General Virology 81:2573–2604, 2000, and Bramson et al., Curr. Opin. Biotechnol. 6:590–595, 1995. Adenovirus vectors have been shown to be capable of highly efficient gene expression in target cells and allow for a large coding capacity of heterologous DNA. Heterologous DNA in this context may be defined as any nucleotide sequence or gene which is not native to the Adenovirus. A preferred form of recombinant Adenovirus is a "gutless", "high-capacity", or "helper-dependent" Adenovirus vector which has all viral coding sequences deleted, and contains the viral inverted terminal repeats (ITRs), therapeutic gene (including Fra-1 binding species) sequences (up to 28–32 kb) and the viral DNA packaging sequence. Variants of such recombinant Adenovirus vectors such as vectors containing tissue-specific (e.g., brain) enhancers and promoters operably linked to a nucleic acid encoding a Fra-1 variant, Fra-1 binding species, c-Jun binding species, and antisense constructs are also within the invention. More than one promoter can be present in a vector. Accordingly, more than one heterologous gene can be expressed by a vector. Further, the vector can include a sequence which facilitates the localization of the Fra-1 variant, Fra-1 binding species, and c-Jun binding species proteins and antisense constructs to the nucleus of the cell, for example.

The viral vectors of the present invention can also include Adeno-Associated Virus (AAV) vectors. AAV exhibits a high transduction efficiency of target cells and can integrate into the host genome in a site-specific manner. Methods for use of recombinant AAV vectors are discussed, for example, in Tal, J., J. Biomed. Sci. 7:279–291, 2000 and Monahan and Samulski, Gene Therapy 7:24–30, 2000. A preferred AAV vector comprises a pair of AAV inverted terminal repeats which flank at least one cassette containing a promoter which directs tissue (e.g., brain) or cell-specific (e.g., astrocytoma) expression operably linked to a nucleic acid encoding a Fra-1 variant, Fra-1 binding species, c-Jun binding species, or antisense construct. The DNA sequence of the AAV vector, including the ITRs, the promoter and the anti-angiogenic agent may be integrated into the host genome.

Methods for use of Herpes Simplex Virus (HSV) vectors are discussed, for example, in Cotter and Robertson, Curr. Opin. Mol. Ther. 1:633–644, 1999. HSV vectors deleted of one or more immediate early genes (IE) are non-cytotoxic, persist in a state similar to latency in the host cell, and afford efficient host cell transduction. Recombinant HSV vectors allow for approximately 30 kb of coding capacity. A preferred HSV vector is engineered from HSV type I, is deleted of the immediate early genes (IE) and contains a tissue-specific (e.g., brain) promoter operably linked to a nucleic acid encoding a Fra-1 variant, Fra-1 binding species, c-Jun binding species, or antisense construct. HSV amplicon vectors may also be used according to the invention. Typically, HSV amplicon vectors are approximately 15 kb in length, possess a viral origin of replication and packaging sequences. More than one promoter can be present in a vector. Accordingly, more than one heterologous gene can be expressed by a vector.

Viral vectors of the present invention may also include replication-defective lentiviral vectors, including HIV. Methods for use of lentiviral vectors are discussed, for example, in Vigna and Naldini, J. Gene Med. 5:308–316, 2000 and Miyoshi et al., J. Virol. 72:8150–8157, 1998. Lentiviral vectors are capable of infecting both dividing and non-dividing cells and efficient transduction of epithelial tissues of humans. HIV vectors have been shown to efficiently infect hepatic cells. Lentiviral vectors according to the invention may be derived from human and non-human (including SIV) lentiviruses. A preferred lentiviral vector of the present invention may include nucleic acid sequences required for vector propagation in addition to a tissue-specific promoter (e.g., brain) operably linked to a nucleic acid encoding a variant Fra-1 protein, Fra-1 binding species, c-Jun binding species or antisense construct. These sequences may include the viral LTRs, primer binding site, polypurine tract, att sites and encapsidation site. The lentiviral vector may be packaged into any suitable lentiviral capsid. The substitution of one particle protein by one from a different virus is referred to as "pseudotyping". The vector capsid may contain viral envelope proteins from other viruses, including Murine Leukemia Virus (MLV) or Vesicular Stomatitis Virus (VSV). The use of the VSV G-protein yields a high vector titer and results in greater stability of the vector virus particles. More than one promoter can be present in a vector. Accordingly, more than one heterologous gene can be expressed by a vector.

The invention also provides for use of retroviral vectors, including Murine Leukemia Virus-based vectors. Methods for use of retrovirus-based vectors are discussed, for example, in Hu and Pathak, Pharmacol. Rev. 52:493–511, 2000 and Fong et al., Crit. Rev. Ther. Drug Carrier Syst. 17:1–60, 2000. Retroviral vectors according to the invention may contain up to 8 kb of heterologous (therapeutic) DNA, in place of the viral genes. Heterologous may be defined in this context as any nucleotide sequence or gene which is not native to the retrovirus. The heterologous DNA may include a tissue-specific promoter, a nucleic acid encoding a variant Fra-1 protein, Fra-1 binding species, c-Jun binding species or antisense construct and may encode a ligand to a brain cell-specific receptor. The retroviral particle may be pseudotyped, and may contain a viral envelope glycoprotein from another virus, in place of the native retroviral glycoprotein. The retroviral vector of the present invention may integrate into the genome of the host cell. More than one promoter can be present in a vector. Accordingly, more than one heterologous gene can be expressed by a vector Other viral vectors within the invention are Alphaviruses, including Semliki Forest Virus (SFV) and Sindbis Virus (SIN). Methods for use of Alphaviruses are described, for example, in Lundstrom, K., Intervirology 43:247–257, 2000 and Perri et al., Journal of Virology 74:9802–9807, 2000. Alphavirus vectors typically are constructed in a format known as a replicon. Such replicons may contain Alphavirus genetic elements required for RNA replication, as well as expression of a nucleic acid encoding a variant Fra-1 protein, Fra-1 binding species, c-Jun binding species or antisense construct. Heterologous may be defined in this context as any nucleotide sequence or gene which is not native to the Alphavirus. Within the Alphivirus replicon, the nucleic acid encoding a variant Fra-1 protein, Fra-1 binding species, c-Jun binding species or antisense construct may be operably linked to a tissue-specific (e.g., brain) promoter or enhancer. Recombinant, replication-defective Alphavirus vectors are capable of high-level heterologous (therapeutic) gene expression, and can infect a wide host cell range. Alphavirus replicons according to the invention may be targeted to specific cell types (e.g., astrocytes) by displaying on their virion surface a functional heterologous ligand or binding domain that would allow selective binding to target cells expressing the cognate binding partner. Alphavirus replicons according to the invention may establish latency, and therefore long-term expression of a nucleic acid encoding a variant Fra-1 protein, Fra-1 binding species, c-Jun binding species or antisense construct in the host cell. The replicons may also exhibit transient expression of a nucleic acid encoding a variant Fra-1 protein, Fra-1 binding species, c-Jun binding species or antisense construct in the host cell. A preferred Alphavirus vector or replicon of the invention is noncytopathic. More than one promoter can be present in a vector. Accordingly, more than one heterologous gene can be expressed by a vector.

To combine advantageous properties of two viral vector systems, hybrid viral vectors may be used to deliver an anti-angiogenic agent to a target tissue (e.g., brain). Standard techniques for the construction of hybrid vectors are well-known to those skilled in the art. Such techniques can be found, for example, in Sambrook, et al., In Molecular Cloning: A laboratory manual. Cold Spring Harbor, N.Y. or any number of laboratory manuals that discuss recombinant DNA technology. Double-stranded AAV genomes in adenoviral capsids containing a combination of AAV and Adenoviral ITRs may be used to transduce cells. In another variation, an AAV vector may be placed into a "gutless", "helper-dependent" or "high-capacity" Adenoviral vector. Adenovirus/AAV hybrid vectors are discussed in Lieber et al., J. Virol. 73:9314–9324, 1999. Retroviral/Adenovirus hybrid vectors are discussed in Zheng et al., Nature Biotechnol. 18:176–186, 2000. Retroviral genomes contained within an Adenovirus may integrate within the host cell genome and effect stable expression of a nucleic acid encoding a variant Fra-1 protein, Fra-1 binding species, c-Jun binding species or antisense construct. More than one promoter can be present in a vector. Accordingly, more than one heterologous gene can be expressed by a vector.

In accordance with the present invention, other nucleotide sequence elements which facilitate expression of the anti-antiangiogenic agent and cloning of the vector are further contemplated. The presence of enhancers upstream of the promoter or terminators downstream of the coding region, for example, can facilitate expression. In the vectors of the present invention, the presence of elements which enhance brain-specific expression of a nucleic acid encoding a Fra-1 protein, Fra-1 binding species, c-Jun binding species or antisense construct may be useful for gene therapy.

Several non-viral methods for introducing an anti-angiogenic agent into host cells are also within the scope of the invention. For a review of non-viral methods, see Nishikawa and Huang, Human Gene Ther. 12:861–870, 2001. Various techniques employing plasmid DNA for the introduction of a nucleic acid encoding a variant Fra-1 protein, Fra-1 binding species, c-Jun binding species or antisense construct into cells may be utilized in methods of the invention. Such techniques are generally known in the art and are described in references such as Ilan, Y., Curr. Opin. Mol. Ther. 1:116–120, 1999, Wolff, J. A., Neuromuscular Disord. 7:314–318, 1997 and Arztl, Z., Fortbild Qualitatssich 92:681–683, 1998.

Methods involving physical techniques for the introduction of an anti-angiogenic agent into a host cell can be adapted for use in the present invention. The particle bombardment method of gene transfer involves an Accell device (gene gun) to accelerate DNA-coated microscopic gold particles into target tissue, including the brain. Particle bombardment methods are described in Yang et al., Mol. Med. Today 2:476–481 1996 and Davidson et al., Rev. Wound Repair Regen. 6:452–459, 2000. Cell electropermeabilization (also termed cell electroporation) may be employed for delivery of a nucleic acid encoding a variant Fra-1 protein, Fra-1 binding species, c-Jun binding species or antisense construct into cells of tissues. This technique is discussed in Preat, V., Ann. Pharm. Fr. 59:239–244 2001 and involves the application of pulsed electric fields to cells to enhance cell permeability, resulting in exogenous polynucleotide transit across the cytoplasmic membrane.

Synthetic gene transfer molecules according to the invention can be designed to form multimolecular aggregates with plasmid DNA (harboring a nucleic acid encoding a variant Fra-1 protein, Fra-1 binding species, c-Jun binding species or antisense construct operably linked to a brain-specific promoter) and to bind the resulting particles to the target cell (e.g., astrocytes) surface in such a way as to trigger endocytosis and endosomal membrane disruption. Polymeric DNA-binding cations (including polylysine, protamine, and cationized albumin) can be linked to astrocyte-specific targeting ligands and trigger receptor-mediated endocytosis into astrocytes. Methods involving polymeric DNA-binding cations are reviewed in Guy et al., Mol. Biotechnol. 3:237–248, 1995 and Garnett, M. C., Crit. Rev. Ther. Drug Carrier Syst. 16:147–207, 1999. Cationic amphiphiles, including lipopolyamines and cationic lipids, may provide receptor-independent transfer of a nucleic acid encoding a variant Fra-1 protein, Fra-1 binding species, c-Jun binding species or antisense construct into target cells (e.g., astrocytes). Preformed cationic liposomes or cationic lipids may be mixed with plasmid DNA to generate cell transfecting complexes. Methods involving cationic lipid formulations are reviewed in Felgner et al., Ann. N.Y. Acad. Sci. 772:126–139, 1995 and Lasic and Templeton, Adv. Drug Delivery Rev. 20:221–266, 1996. Suitable methods can also include use of cationic liposomes as agents for introducing DNA or protein into cells. For therapeutic gene delivery, DNA may also be coupled to an amphipathic cationic peptide (Fominaya et al., J. Gene Med. 2:455–464, 2000).

Methods that involve both viral and non-viral based components may be used according to the invention. An Epstein Barr Virus (EBV) based plasmid for therapeutic gene delivery is described in Cui et al., Gene Therapy 8:1508–1513, 2001. A method involving a DNA/ligand/polycationic adjunct coupled to an Adenovirus is described in Curiel, D. T., Nat. Immun. 13:141–164, 1994. More than one promoter can be present in a vector. Accordingly, more than one heterologous gene can be expressed by a vector.

Other techniques according to the invention may be based on the use of brain-specific ligands. Synthetic peptides or polypeptides may be used as ligands in targeted delivery of DNA and proteins to brain-specific receptors. Complexes of protein and ligand or plasmid DNA and ligand mediate protein and DNA transfer into brain cells.

Methods involving ultrasound contrast agent delivery vehicles may be used in the invention. Such methods are discussed in Newman et al., Echocardiography 18:339–347, 2001 and Lewin et al. Invest. Radiol. 36:9–14, 2001. Gene-bearing microbubbles, when exposed to ultrasound, cavitate and locally release a therapeutic agent. Attachment of a brain cell-targeting moiety to the contrast agent vehicle may result in site-specific (e.g., brain) expression of a nucleic acid encoding a variant Fra-1 protein, Fra-1 binding species, c-Jun binding species or antisense construct.

Methods which are well known to those skilled in the art can be used to construct a natural or synthetic matrix that provides support for the delivered agent (e.g., an anti-angiogenic agent) prior to delivery. See, for example, the techniques described in Murphy and Mooney, J. Period Res., 34:413–9, 1999 and Vercruysse and Prestwich, Crit. Rev. Ther. Drug Carrier Syst., 15:513–55, 1998. The particular type of matrix used can be any suitable matrix for use in the invention. For implantation into an animal subject, preferred matrix will have all the features commonly associated with being "biocompatible", in that they do not produce an adverse, or allergic reaction when administered to the recipient host. Matrices suitable for use in the invention may be formed from both natural or synthetic materials and may be designed to allow for sustained release of the therapeutic agent and growth factors over prolonged periods of time. Thus, appropriate matrices will both provide anti-angiogenic factors and also act as an in situ scaffolding for the delivered agent (e.g., a nucleic acid encoding a variant Fra-1 protein, Fra-1 binding species, c-Jun binding species or antisense construct). Preferred matrices are those that are biodegradable as these are capable of being reabsorbed.

Delivery of an anti-angiogenic agent, according to the invention, may involve methods of DNA microencapsulation. Microparticles, also known as microcapsules and microspheres, may be used as gene delivery vehicles. They may be delivered in operable form noninvasively to epithelial surfaces for gene therapy. The genes within the microparticles can pass across epithelial barriers and travel to remote sites, via systemic circulation. Microencapsulated gene delivery vehicles may be constructed from low viscosity polymer solutions that are forced to phase invert into fragmented spherical polymer particles when added to appropriate nonsolvents. Methods involving microparticles are discussed in Hsu et al., J. Drug Target 7:313–323, 1999 and Capan et al., Pharm. Res. 16:509–513, 1999.

Methods involving microencapsulated recombinant cells may be used in the invention. Such an approach may be used in either in vivo or ex vivo techniques. Cells that contain an expression vector coding for a nucleic acid encoding a variant Fra-1 protein, Fra-1 binding species, c-Jun binding species or antisense construct or that have been engineered to stably express a nucleic acid encoding a variant Fra-1 protein, Fra-1 binding species, c-Jun binding species or antisense construct may be encapsulated in microcapsules that provide protection from immune mediators and allow appropriate release of the anti-angiogenic agent. Preferred microencapsulation particles, also referred to as encapsulation devices, consist of biocompatible and biodegradable components. Techniques involving microencapsulated cells are discussed in Ross et al. Hum. Gen. Ther. 11:2117–2127, 2000 and Fong et al., Crit. Rev. Ther. Drug Carrier Syst. 17:1–60, 2000.

Protein transduction offers an alternative to gene therapy for the delivery of therapeutic proteins into target cells, and methods of protein transduction are within the scope of the invention. Protein transduction is the internalization of proteins into a host cell, from the external environment. The internalization process relies on a protein or peptide which is able to penetrate the cell membrane. The transducing property of such a protein or peptide can be conferred upon proteins (Fra-1 variant, Fra-1 binding species, and a c-Jun binding species, for example) which are expressed as fusion proteins with them. Commonly used protein transduction vehicles include the antennapedia peptide, the HIV TAT protein transduction domain and the herpes simplex virus VP22 protein. Such vehicles are reviewed in Ford et al., Gene Ther. 8:1–4, 2001.

Method for Identifying a Test Compound that Modulates Fra-1 Gene Expression

The invention provides for a method of identifying a test compound that modulates expression of a Fra-1 gene in a brain cancer cell. One such method involves providing a cell that expresses Fra-1 and at least one test compound, contacting the cell with the test compound, and detecting whether or not the test compound modulates Fra-1 expression. Those compounds resulting specifically in altered levels (increased or decreased levels) of Fra-1 protein are those that specifically modulate Fra-1 expression. For example, a library of molecules can be screened by providing brain cancer cells expressing Fra-1 and contacting the cells with the library and examining the cells for changes in Fra-1 expression. Changes in Fra-1 expression may be assessed by analyzing changes in Fra-1 marker (e.g. Fra-1 protein and Fra-1 mRNA) levels.

Disruption of Fra-1/c-JUN-VEGF-D Promoter Interactions

Nucleic acids encoding binding mutants as well as binding mutant proteins may be used in methods of the invention to interfere with binding of Fra-1 and/or c-Jun to the VEGF-D gene promoter. Such molecules include a variant Fra-1 protein that binds to native c-Jun yet lacks the ability to bind the VEGF-D promoter. An example of such a variant is a dominant negative mutant of Fra-1 which dimerizes with native c-Jun and blocks binding of the dimer to a VEGF-D promoter. Similarly, an example of another variant is a dominant negative mutant of c-Jun which dimerizes with native Fra-1 and blocks binding of the dimer to a VEGF-D promoter. Alternatively, nucleic acids themselves may be used to disrupt the binding of these transcription factors to the VEGF-D promoter. For example, over-expression of a high copy plasmid harboring an excess of AP-1 binding sites (i.e. VEGF-D promoter binding sites) would bind Fra-1 and sequester Fra-1 from the native VEGF-D promoter. The mutagenic techniques described herein can be used to map which determinants of Fra-1 and c-Jun proteins participate in the intermolecular interactions involved in, for example, binding of Fra-1 or c-Jun to a VEGF-D promoter.

Fra-1 and c-Jun protein variants that do not bind a VEGF-D promoter can be generated through various techniques known in the art. For example, Fra-1 and c-Jun protein variants can be made by mutagenesis, such as by introducing discrete point mutation(s), by insertion or deletion. Whether a change in the amino acid sequence of a peptide results in a Fra-1 or c-Jun protein variant lacking one or more functional activities of a native Fra-1 or c-Jun protein can be readily determined by testing the variant for a native Fra-1 or c-Jun protein functional activity. For example, a brain tissue sample containing a VEGF-D promoter receptor can be contacted with a Fra-1 or c-Jun protein variant that lacks the ability to bind the promoter. The brain tissue sample can then be analyzed for VEGF-D gene expression as well as angiogenesis.

Inhibiting Angiogenesis

The invention provides a method for inhibiting angiogenesis associated with a brain cancer in a subject by providing an agent that interferes with Fra-1 binding to a VEGF-D gene promoter and administering the agent to the central nervous system of the subject. The agent would be administered in an amount effective to inhibit blood vessel development associated with cancer. For example, VEGF-D expression in a brain cell may be inhibited by introducing into the cell an agent that interferes with activation of the VEGF-D gene by Fra-1. Such an agent can be an oligonucleotide (e.g., antisense oligonucleotide) that hybridizes to a polynucleotide that encodes a Fra-1 protein. In another embodiment, the agent may be a protein that binds Fra-1 and precludes the interaction of Fra-1 with its binding partner c-Jun.

Administration of Compositions

The compositions described above may be administered to animals including human beings in any suitable formulation. For example, anti-angiogenic molecules may be formulated in pharmaceutically acceptable carriers or diluents such as physiological saline or a buffered salt solution. Suitable carriers and diluents can be selected on the basis of mode and route of administration and standard pharmaceutical practice. A description of exemplary pharmaceutically acceptable carriers and diluents, as well as pharmaceutical formulations, can be found in Remington's Pharmaceutical Sciences, a standard text in this field, and in USP/NF. Other substances may be added to the compositions to stabilize and/or preserve the compositions.

The compositions of the invention may be administered to animals by any conventional technique. The compositions may be administered directly to a target site by, for example, surgical delivery to an internal or external target site, or by catheter to a site accessible by a blood vessel. Other methods of delivery, e.g., liposomal delivery or diffusion from a device impregnated with the composition, are known in the art. The compositions may be administered in a single bolus, multiple injections, or by continuous infusion (e.g., intravenously). For parenteral administration, the compositions are preferably formulated in a sterilized pyrogen-free form.

Systemic (i.v.) with local interstitial drug delivery may be used according to the invention. The concept of convection enhanced delivery is becoming more attractive as an effective route of drug delivery into the brain. Laske et al., Nature Medicine 3, 1362–1368 (1997). Consequently, local delivery is the preferred approach to be evaluated clinically, since it may achieve high concentrations directly within the tumor mass and its vicinity.

Generally, compositions used in methods of the invention are introduced into a tumor cell using in vivo transduction techniques. Particularly, for in vivo delivery, the compositions will be formulated into pharmaceutical compositions and generally administered by direct injection into a tumor mass, injected intravenously into blood veins feeding the tumor mass, or administered into a tumor bed subsequent to tumor resection.

The compositions used in the invention may be precisely delivered into tumor sites, e.g., into gliomas or other intracranial tumors, by using stereotactic microinjection techniques. For example, the mammalian subject to be treated can be placed within a stereotactic frame base that is MRI-compatible and then imaged using high resolution MRI to determine the three-dimensional positioning of the particular tumor being treated. According to this technique, the MRI images are then transferred to a computer having the appropriate stereotactic software, and a number of images are used to determine a target site and trajectory for anti-angiogenic composition microinjection. Using such software, the trajectory is translated into three-dimensional coordinates appropriate for the stereotactic frame. For intracranial delivery, the skull will be exposed, burr holes will be drilled above the entry site, and the stereotactic apparatus positioned with the needle implanted at a predetermined depth. Tumor resection operations may be carried out prior to positioning of the stereotactic apparatus, if desired. A pharmaceutical composition containing an anti-angiogenic agent according to the invention can then be microinjected at the selected target site(s).

Effective Doses

The compositions described above are preferably administered to a mammal in an effective amount, that is, an amount capable of producing a desirable result in a treated subject (e.g., inhibiting angiogenesis and treating malignant tumors in the subject). Such a therapeutically effective amount can be determined as described below.

Toxicity and therapeutic efficacy of the compositions utilized in methods of the invention can be determined by standard pharmaceutical procedures, using either cells in culture or experimental animals to determine the $LD_{50}$ (the dose lethal to 50% of the population). The dose ratio between toxic and therapeutic effects is the therapeutic index and it can be expressed as the ratio $LD_{50}/ED_{50}$. Those compositions that exhibit large therapeutic indices are preferred. While those that exhibit toxic side effects may be used, care should be taken to design a delivery system that minimizes the potential damage of such side effects. The dosage of preferred compositions lies preferably within a range that includes an $ED_{50}$ with little or no toxicity. The dosage may vary within this range depending upon the dosage form employed and the route of administration utilized.

As is known in the medical and veterinary arts, dosage for any one animal depends on many factors, including the subject's size, body surface area, age, the particular composition to be administered, time and route of administration, general health, and other drugs being administered concurrently. It is expected that an appropriate dosage for intratumoral administration of the compositions would be in the range of about 0.001 to 100 mg/kg body weight.

EXAMPLES

The present invention is further illustrated by the following specific examples. The examples are provided for illustration only and are not to be construed as limiting the scope or content of the invention in any way.

Example 1

Material and Methods

Cell lines and tissues: Glioblastoma multiforme cells lines A172 MG, U-251 MG, DBTRG-50 MG, U-87 MG, U-373 MG, human GBM explant cells, G48a, CSML0 and CSML100 mouse breast carcinoma cells were grown in appropriate media. The CSML0 CSML100 mouse breat cancer cells and GBM A172 MG glioblastoma cells were grown in Dulbecco's Modified Eagle's Medium (D-MEM) with 10% Fetal Calf Serum (FCS) (Life Technologies, Rockville, Md.). U-251 MG cells were grown in D-MEM, 10% FCS, 0.1 mM MEM Non-Essential Amino Acids (NEAA) (Life Technologies), and 50 µg/ml Gentamicin Sulfate. GBM cell lines U-87 MG and U-373 MG were grown in Earle's Minimum Essential Medium (MEM), 10% FCS, 0.1 nM NEAA, 2 mM Glutamine (Life Technologies), and 100 µg/ml Sodium Pyruvate. GMB cell line DBTRG-50 MG and human explant cells were grown in RPMI-1640 (Life Technologies) 10% FCS, 100 µg/ml Sodium Pyruvate, / 100 µg/ml L-Cystine (Life Technologies), 20 µg/ml L-Proline (Sigma), 1×HT Supplement, consisting of 0.1 µM Sodium Hypoxanthine and 0.016 µM Thymindine, 5 units/ml Pennicilin G and 5 units/ml Streptomycin sulfate (Penn/Strep) (Life Technologies). Noral Human Astrocytes (NHA) were grown in Astrocyte Growth Medium BulletKit® (BioWhittaker). Normal HUV-EC-C were grown in F-12 Kaighn's medium (Life Technologies) with 10% FCS, 100 µg/ml Heparin (Sigma) and 30 µg/ml Endothelial Cell Growth Supplement (ECGS) (Sigma).

A retroviral vector was used to generate plasmid pMVFra-1. To produce replication-defective retroviruses, the GP+E packaging cell line was employed, which was maintained in appropriate media. Successfully transfected GP+E cells were selected in the presence of 800 µg/ml G418. Supernatants of virus-producing cell lines were used to infect CSML0 cells. Infected cells were selected in the presence of 400 µg/ml G418.

GBM tumors and non-malignant brain tissue, the latter obtained usually from the therapeutic resections for the treatment of epilepsy, were obtained from the operating room and snap frozen immediately, as described previously. Debinski et al. (1999) Clin. Cancer Res. 5:985–990. Ten-micron sections of GBM were thaw-mounted onto chrom-alum slides. Slides were stored at –80° C. until assayed. Sections were allowed to thaw and subsequently fixed for 10 min in acetone at –20° C.

Immunostaining: GBM cells lines, human explant cells (G48a), Human Umbilical Vein Endothelial Cells (HUV-EC-C) from ATCC (Rockville, Md.), and normal human astrocytes (NHA) from BioWhittaker (Walkersville, Md.) were grown overnight on sterile glass slides in the appropriate media. Slides were washed twice in PBS and fixed for 2 min in acetone at –80° C. Slides were washed twice in PBS and either used immediately or air-dried and stored at –80° C. until assayed. In stimulation experiments, $10^4$ SNB-19

GBM cells were plated on glass chamber slides and allowed to attach overnight. The cells were washed with PBS and serum-free media was applied. After 24 hr epidermal growth factor (EGF) or leukemia inhibitory factor (LIF) were added to cells at 5 and 20 ng/ml, respectively. The cells were processed for immunocytochemistry after 24 hr of stimulation period.

Mouse monoclonal anti-VEGF-D (VD1) antibody was used. See, Achen et al. (2000) Eur. J. Biochem. 267: 2505–2515. It was employed at a final dilution of 1:500 (7.5 µg/ml). Other primary antibodies including rabbit polyclonal Fra-1 (1:100), c-Fos (1:100), c-Jun (1:150), and mouse monoclonal JunB (1:75) were purchased from Santa Cruz Biotechnology (Santa Cruz, Calif.); and mouse monoclonal Factor VIII (1:150) and rabbit GFAP (1:500) were purchased from DAKO Chemical (Carpinteria, Calif.).

Slides were washed in two changes of PBS and blocked for 30 min with 10% (v/v) normal goat serum (NGS) in PBS at room temperature. Primary antibody was diluted in 1.5% NGS/PBS and incubated at room temperature for either 1 hr (VEGF-D, Factor VIII, and GFAP) or 2 hr (Fra-1, JunB, c-Fos, and c-Jun). Slides were washed in three changes of PBS for 10 min each. Secondary antibody, goat anti-rabbit Rhodamine (1:150), Jackson ImmunoResearch Laboratories, Inc. (West Grove, Pa.) or sheep anti-mouse Cy3 (1:250), Sigma (St. Louis, Mo.) was diluted in 1.5% NGS/PBS and incubated in the dark at room temperature for 45 min. For double-labeling experiments, the secondary antibodies were goat anti-mouse Oregon Green$^R$ (:200) (Molecular Probes, Oregon) and goat anti-rabbit Rhodamine (: 150). Slides were washed in 3 changes of PBS for 10 min each and mounted with Gel-Mount, Biomeda Corp. (Foster City, Calif.). Some slides were counterstained with Hoechst No. 33258 Nuclear Counterstain (DAPI).

Photomicrographs were taken at 40× magnification in all cases with a Hamamatsu C2400 digital camera. Background was normalized to the samples without primary antibody. Each set of images was taken exactly at the same exposure settings. Images were processed with Paint Shop Pro V 6.0 (Jasc software Inc., Eden Prairie, Minn.).

Western Blots: Cell lysates were prepared from sub-confluent cultures. Cells were washed twice in PBS and lysed in RIPA buffer (PBS, 1% Igepal CA-630; ICN Biomedicals, Inc. Costa Mesa, Calif.), 0.5% sodium deoxycholate (Fisher Scientific, Fair lawn, N.J.), 0.1% SDS containing Mammalian Protease Inhibitor Cocktail (Sigma). GBM and non-malignant brain tumor samples were minced into small pieces while frozen and thawed in RIPA buffer with Mammalian Protease Inhibitor Cocktail. Lysates were passed through a 21-gauge needle to shear the DNA. 1 mM PMSF (Sigma) was added and the lysates were incubated on ice for 30–60 min. Non-solubilized debris was pelleted at 10,000×g for 10 min. The supernatant was collected, aliquoted, and stored at −80° C. until use. Normal human brain lysates were also purchased from Chemicon International, Inc. (Temecula, Calif.) and Clontech.

Lysates were run on either 12% or 15% SDS-PAGE. Proteins were transferred to PVDF membrane (Pierce, Rockford, Ill.) and blocked for 1 hr with 5% blotto (5% dry milk, PBS, 0.05% Tween-20). Membranes were incubated with primary antibody diluted in blotto for 40 min at room temperature while shaking. Antibodies included: anti-mouse VEGF-D antibody (40% cross-reactivity with human VEGF-D; 1:500) from R&D Systems, and Fra-1 (1:100) from Santa Cruz Research Antibodies. Following three five-minute washes in PBS/0.05% Tween-20, membranes were incubated in secondary antibody conjugated with horseradish peroxidase (goat anti-mouse IgG or goat anti-rabbit IgG) at a dilution of 1:10,000 or 1:15,000 in 5% blotto for 40 min at room temperature while shaking. Membranes were washed in several changes of PBS and detection was performed using the SuperSignal West Pico Chemiluminescent Substrate (Pierce). Membranes were exposed to autoradiographic film X-OMAT AR for up to 5 min. Films were scanned in a transparency scanner at a pixel size of 88×88 micron (Molecular Dynamics, Sunnyvale, Calif.). The images were compiled in Paint Shop Pro V 6.0.

cDNA arrays: Atlas Oncogene/Tumor Suppressor Arrays were purchased from Clontech and 1 µg of poly(A)+RNA was labeled with [α-$^{33}$P]dATP according to the manufacturer. Membranes were pre-hybridized overnight at 68° C. in ExpressHyb (Clontech) containing 0.1 mg/ml sheared salmon sperm DNA. Labeled cDNA probe was denatured and added to the pre-hybridization solution and the membranes were hybridized overnight at 68° C. Membranes were then washed twice in 2×SSC/1% SDS for 20 min followed by two washes in 0.1% SSC/0.5% SDS at 68° C. The membranes were exposed to autoradiographic film for up to 10 days at −70° C. The arrays contain cDNA specific fragments for oncogenes, such as c-fos, junB, and c-myc. Housekeeping genes included ubiquitin, liver glyceraldehyde 3-phosphate dehydrogenase (GAPDH), and phospholipase. RNA used for the cDNA micro-array assays was isolated from sub-confluent cultures of GBM cells using the acid-guanidium isothiocyanate-phenol-chloroform method. Chomczynski P, and Sacchi N (1987) Analyt. Biochem. 162: 156–159. Poly(A)+RNA was further isolated using the Oligotex mRNA Kit (Qiagen Inc, Valencia, Calif.). Normal Human Brain Poly(A)+RNA was purchased from Clontech (Clontech Laboratories, Inc., Palo Alto, Calif.).

Karyotyping: The karyotypes of HGA cells analyzed in this study were performed in a blinded fashion by clinical cytogeneticists at the Cancer Genetics Laboratory, Genetics & IVF Institute, Fairfax, Va.

Example 2

Fos Transcription Factors in GBM Cells

VEGF-D has been reported as a c-fos inducible mitogenic and morphogenic factor, and named accordingly a c-fos-induced growth factor (FIGF). It was thus imperative to explore the c-fos oncogene protein expression in GBM, since it was the foremost suspect responsible for high and ubiquitous over-expression of VEGF-D. Contrary to what one would expect, the levels of c-Fos in several GBM cell lines were found to be low. Specific nuclear immunoreactivity for c-Fos was seen mainly in some of the DBTRG-50 MG cells. Others found similarly low levels of c-fos gene expression in brain tumor cells. Thus, different factors than c-Fos may be involved in sustained VEGF-D up-regulation in GBM cells.

The gene for VEGF-D has an optimal AP-1 binding site in its promoter region. Considering the lack of correlation between the levels of c-Fos and VEGF-D in GBM cells, the possibility that other AP-1 transcription factors, to which c-Fos belongs, play roles in VEGF-D up-regulation was explored. Experiments with oncogene/tumor suppressor gene-containing EDNA microarrays revealed that the expression of the fos-related antigen-1 gene (Fra-1) is higher in GBM cells, such as G48a, when compared with normal brain tissue, while the expression of c-fos was usually undetectable. The same phenomenon was observed in DBTRG-50 MG and U-87 MG GBM cell lines. Therefore, immunofluorescence using anti-Fra-1 antibody was performed in GBM cells. It was discovered that Fra-1 is highly expressed in all GBM cell lines studied, such as G48a, U-87 MG, U-251 MG, and DBTRG-50 MG. However, the pattern of staining for Fra-1 was distinctly different from the rather diffuse cytoplasmic staining seen for VEGF-D. Anti-Fra-1 immunopositivity was localized to the nuclei of the cells, which would be expected for this transcription factor. HUV-EC-C demonstrated limited nuclear immunofluorescence for Fra-1. Western blot analysis was performed on GBM cell lysates and tumor samples and revealed a protein band of ~42 kDa, which corresponds to the size of human Fra-1.

Fra-1 cannot activate gene expression itself, since it requires heterodimerization with Jun proteins to do so. c-Jun and JunB in particular are preferable partners for Fra-1 and, in the process of Fra-1 up-regulation in response to Ras activation, c-Jun was primarily utilized as the binding partner with Fra-1. Based on cDNA microarray analyses, c-jun, and much less junB, was found expressed in astrocytoma cells. In follow-up immunohistochemical studies, the staining for c-Jun was readily detected and localized to the nuclei of GBM cells, similar to the Fra-1 staining. JunB was detected by immunohistochemistry although at lower intensities than c-Jun. Interestingly, c-jun was the only gene expressed in normal brain tissue among AP-1 factors.

Example 3

Fra-1 Induces Expression of VEGF-D

Studies have focused on Fra-1 and its role in transcriptional activation of other factors which are likely suspects involved in cancer progression/maintenance. For example, Fra-1 has been previously identified as the primary AP-1 factor involved in the development of a more invasive, highly progressive carcinoma phenotype of breast cancer. Immunoblot analysis for VEGF-D was therefore performed in cell lysates of CSML0 (low Fra-1) and CSML100 (high Fra-1) mouse breast cancer cells. Elevated levels of VEGF-D were observed in CSML100 when compared with CSML0 cells. Furthermore, mock-transfected and Fra-1-transfected CSML0 cells were utilized. The mock-transfected CSML0 cells did not express Fra-1, as expected, and showed no VEGF-D immunoreactivity, whereas the Fra-1 transgene evoked VEGF-D expression in transfected CSML0 cells. The size of the detected band was ~33 kDa, which corresponds to a form of murine VEGF-D, consisting most probably of the N-terminal pro-peptide and the VEGF homology domain, that is found in VEGF-D-producing organs, such as heart and in VEGF-D-producing cells, such as fibroblasts. Thus, Fra-1 expression converts cells to VEGF-D producers.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of identifying a test compound that modulates expression of a Fra-1 gene in a brain cancer cell, the method comprising the steps of:

(A) providing a brain cancer cell expressing a Fra-1 gene;
   (B) contacting the cell with the test compound; and
   (C) detecting a modulation in the expression of the Fra-1 gene, wherein detecting the modulation indicates that the test compound modulates expression of the Fra-1 gene.

2. The method of claim 1, wherein the cell is derived from a tissue sample isolated from a human brain.

3. The method of claim 1, wherein the step of detecting the modulation in the expression of the Fra-1 gene comprises analyzing the cell for a change in the amount of a Fra-1 marker in the cell.

4. The method of claim 3, wherein the Fra-1 marker is a Fra-1 nucleic acid.

5. The method of claim 4, wherein the Fra-1 nucleic acid is an RNA.

6. The method of claim 4, wherein the Fra-1 nucleic acid is a native Fra-1 nucleic acid.

7. The method of claim 3, wherein the Fra-1 marker is a Fra-1 protein.

8. The method of claim 7, wherein the Fra-1 protein is a native Fra-1 protein.

* * * * *